Figure 4:
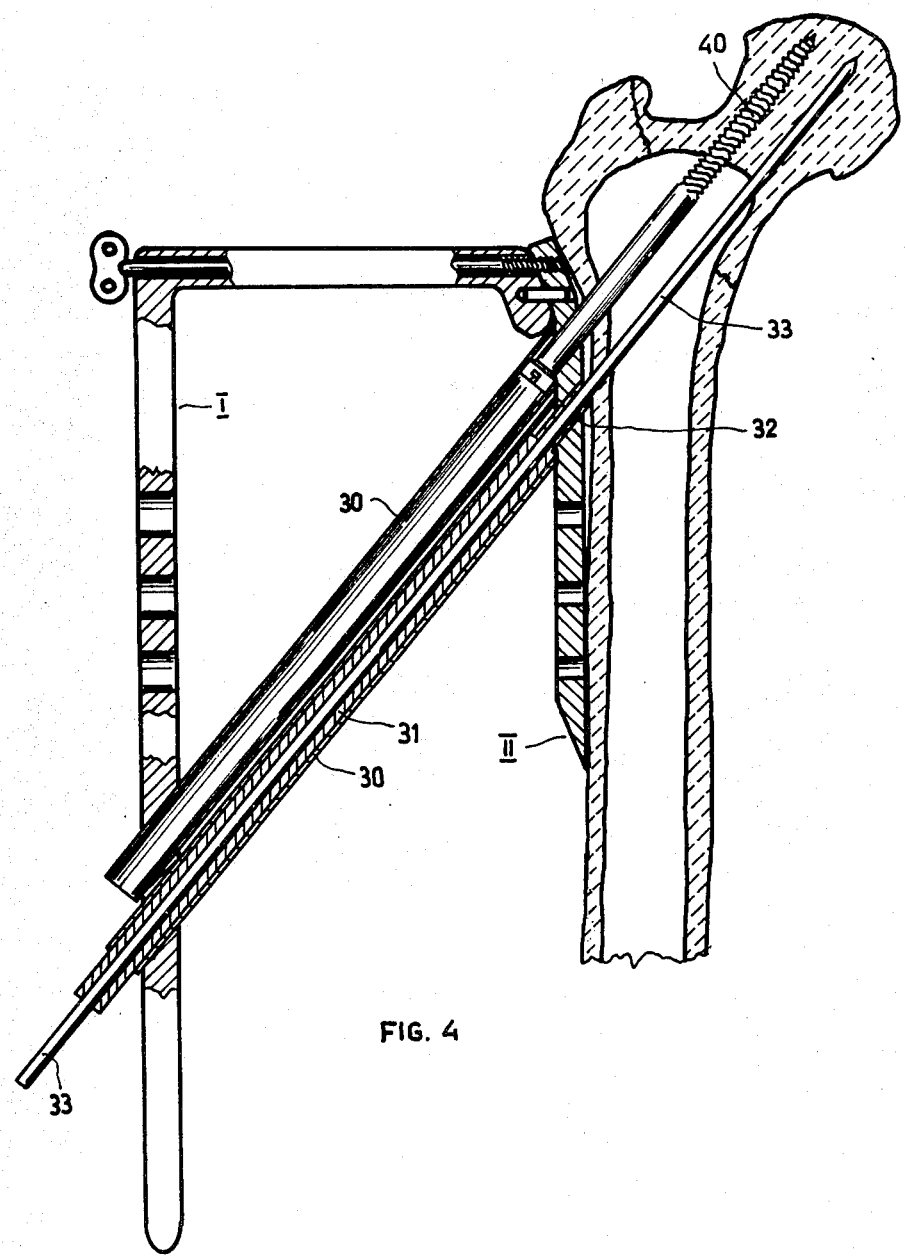

United States Patent [19]

Gotfried

[11] Patent Number: 4,465,065

[45] Date of Patent: Aug. 14, 1984

[54] SURGICAL DEVICE FOR CONNECTION OF FRACTURED BONES

[76] Inventor: Yechiel Gotfried, 10, Ben-Gurion Ave., Kiriat Bialik, Israel

[21] Appl. No.: 456,403

[22] Filed: Jan. 7, 1983

[51] Int. Cl.³ .......................... A61F 5/04; A61B 17/18
[52] U.S. Cl. .............................. 128/92 BB; 128/92 B; 128/92 A; 128/92 EB
[58] Field of Search ............ 128/92 BB, 92 BA, 92 B, 128/92 EA, 92 EB, 92 A, 92 D, 92 R, 83

[56] References Cited

U.S. PATENT DOCUMENTS

| | | | |
|---|---|---|---|
| 3,094,120 | 6/1963 | Blosser | 128/92 BB |
| 3,782,374 | 1/1974 | Fischer | 128/92 BB |
| 4,103,683 | 8/1978 | Neufeld | 128/92 BA |
| 4,381,770 | 5/1983 | Neufeld | 128/92 BA |

FOREIGN PATENT DOCUMENTS 2406430  6/1979  France .......................... 128/92 BB Primary Examiner—Ronald L. Frinks
Attorney, Agent, or Firm—John S. Roberts, Jr.

[57] ABSTRACT

An L-shaped surgical device serves for the connection of a fractured neck to the shaft of a femur by means of a pre-drilled connector plate, without the requirement of making a large incision in the overlying skin and tissue. The connector plate has a sharp lower edge by which it penetrates through a small incision in the trochanter region into close contact with the shaft. During the operation the upper end of the plate is temporarily attached to the horizontal arm of the device, while its vertical arm extends parallel to the plate and is provided with holes in continuation of the holes in the plate. Guide tubes are provided which extend through the holes in the arm to the holes in the plate after having been pushed through the soft tissue. The tubes serve as guides for pre-drilling of the bone parts on the correct position as viewed by X-ray equipment, and subsequently for the insertion of long screws and fixation of the broken parts by tightening of the screws. The guide tubes are subsequently withdrawn and the device is detached from the connector plate which remains inside the tissue connected to the bone by the screws.

9 Claims, 8 Drawing Figures

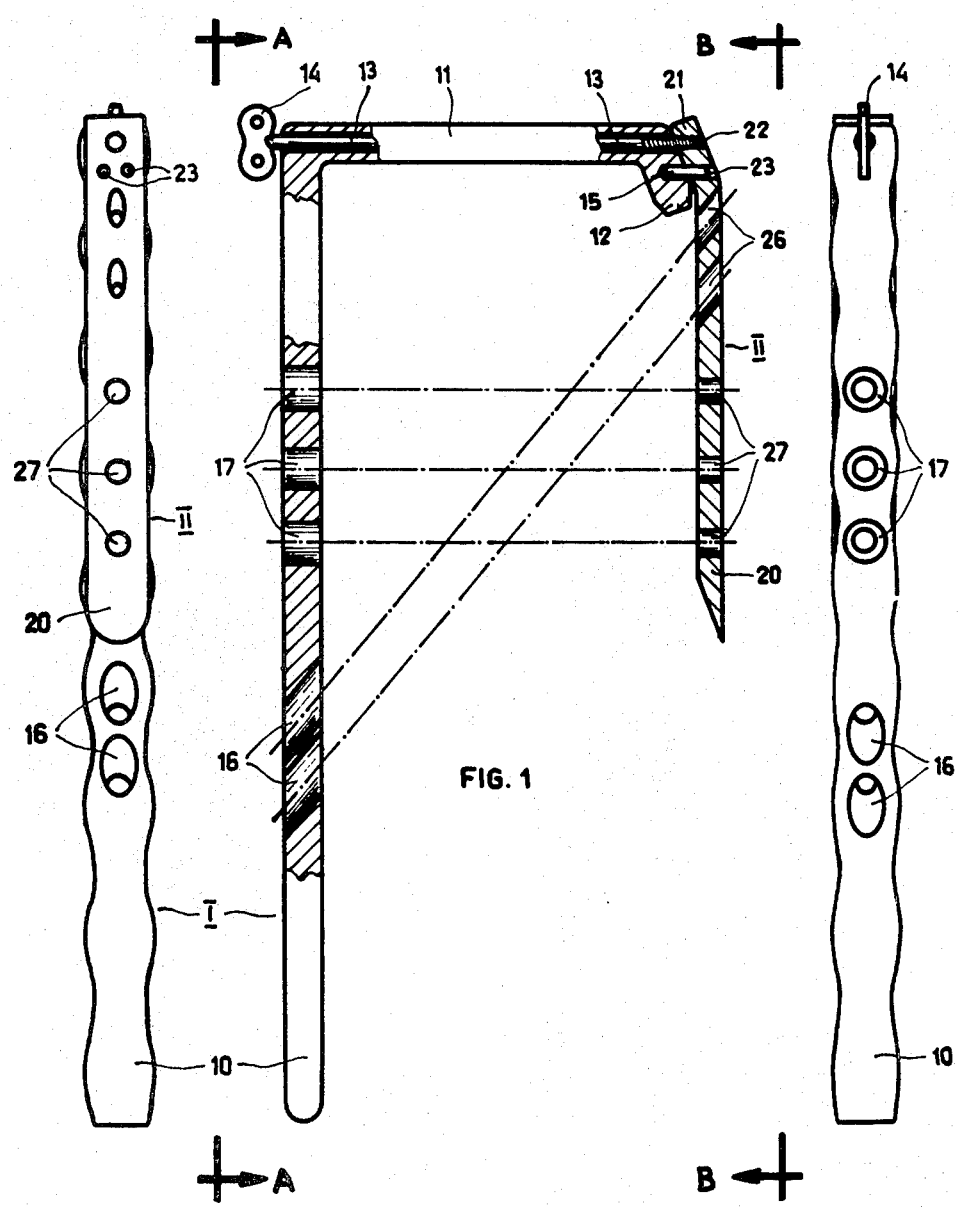

SURGICAL DEVICE FOR CONNECTION OF FRACTURED BONES

The invention relates to the setting of fractured bones, more especially to the setting and connecting of a fractured neck in the trochanteric region and the femur, without the necessity to expose the bone through a long and wide incision in the overlying tissue and skin.

It is known to connect a fractured neck of a femur by placing a pre-drilled fixator plate on to the femur shaft, to drill holes through the shaft into the end of the spherical head of the femur, and to drive one or two screws through the plate into the firm bone, thus compressing the fractured edges of the separated parts for quick healing in their correct alignment. The plate is fixed in rigid position on the shaft by two or more screws passing through the fixator plate and through the bone material. Since the plate is comparatively long (about 130 mm.), with a view to hold the fractured parts in rigid alignment, a large incision has to be made in the tissue and skin overlying the femur, usually requiring general epidural or opinal anesthesis of the patient. As a consequence of this large incision much loss of blood and a long healing period are experienced, and it is, therefore, desired to carry out this kind of operation by minimizing the area and volume to be opened, and to endeavour to insert the screws through small cuts in the skin, without total exposition of the bone area. This would permit performing the operation by application of local anesthization to the affected area only, an important point with patients suffering from a heart disease or being otherwise unable to undergo full anesthesizing.

The main difficulty encountered with such percutaneous operation is the correct positioning of the fixator plate and the insertion of the screws to the correct depth and at the required angle. At present operations of this kind are performed by viewing the bone and the metal inserts on a television screen, whereby the light source and the sensor can be moved around the wounded limb in order to view it from all angles; however, this aid does not absolve the surgeon from exposing the entire upper portion of the femur by cutting the skin and the soft tissue, in order to position the fixator plate.

It is, therefore, the main object to provide an auxiliary device which will enable the surgeon to position the fixator plate in the correct position on the femur shaft, through a relatively small incision in the skin, to drill the bone for the reception of the connecting screws, and to enable insertion and tightening of the screws for compression and fixation of the fractured bone parts, through small incisions in the skin. It is a further object to provide a standard auxiliary device which is not destined for single use, but should be utilized in respect of many patients suffering from similar fractures of the upper femur. It is still another object to provide the device with means for viewing the direction of the connector screws from the outside of the body, again without the necessity of exposing the bone.

The surgical device according to the present invention fulfills the requirements which have been outlined above.

Before going into constructional details of the device, it should be noted that the following directional expressions will be employed in respect of the femur bone, the tool, the fixator plate and the screws used during the operation in order to connect the fractured parts: the expressions "top" or "upper portion" of any part will refer to the direction of the femur top, and the "bottom" or "lower portion" will refer to the direction towards the knee joint. The expression "inside" or "inner portion" will refer to parts close to the bone outside or pointing towards it, while the expressions "outside" or "outer portion" will refer to those parts which are outside the human body operated on, or pointing away from the bone.

The surgical device is adapted to be connected to a pre-drilled fixator plate of rectangular cross section, which has a substantially straight main portion and a short, upper portion outwardly bent so as to conform to the contour of the bone. The lower end of the fixator plate has a sharp rounded chisel edge permitting its penetration through the tissue covering the bone shaft.

The auxiliary device itself comprises a rigid angle-shaped tool adapted to be attached to the upper end of the above fixator plate by screw means which can be released after a completed operation. The tool comprises a first arm serving as a handle or grip which is substantially parallel to the fixator plate—in its connected state—, and a second connector arm at the tool top which is substantially perpendicular to the first arm and is provided with screw means for rigidly attaching to its inner end the top end of the fixator plate.

Both the tool grip and the fixator plate are provided with a number of co-axially aligned bores, which are of larger diameter in the grip and of smaller diameter in the plate. They comprise two obliquely directed, parallel bores forming an angle of about 140° with the plane of the fixator plate which penetrate through the fixator plate close to its bent upper portion and through the grip close to its bottom end. They further comprise two or more parallel bores, similarly passing through the grip and through the plate in co-axial alignment which are substantially perpendicular to the plane of the plate, both the oblique and the perpendicular bores lying on the centre lines of both the grip and the plate.

The device also comprises, in addition to the gripping tool, tubular guide assemblies serving to guide drills and screws into the bone. Each assembly comprises an outer guide in the form of a tube having an outer diameter corresponding to the bore diameter in the grip and an inner diameter corresponding to the diameter of the screw head, permitting its passage there through; each assembly further comprises an inner guide in the form of a tube of an outer diameter corresponding to the inner diameter of the outer guide, which is reduced at the inner end, to the diameter of the bore in the fixator plate, and of an inner diameter corresponding to the diameter of a thin drill rod or guide wire, the latter being used for insertion into the bone, for controlling the eventual direction and position of the screws by means of X-ray viewing.

Connection between the top of the fixator plate and the end of the connector arm is preferably made by a long screw passing along the arm into a tapped bore in the bent top portion of the plate; additional fixation against mutual rotation about the screw axis is made by means of one or two pins projecting out of the arm end and engaging with corresponding holes in the plate top.

An operation with the aid of the device is carried out in the following stages: a fixator plate of dimensions suitable for the specific fractured femur is firmly attached to the angular tool; the fracture and the area to be operated on are locally anesthetized, and an incision is made into the skin somewhat above the trochanter portion; the plate is inserted through the incision with its sharp chisel end first, while the tool grip remains outside of the thigh; by pressing and moving the tool, the plate is brought into position close to the bone by cutting through the soft tissue, the correct position being continuously controlled by X-ray viewing. Now an outer tubular guide is inserted into one of the oblique bores in the tool grip, and an incision is made in the skin at the point where the guide end meets it; a trocar is inserted into the tubular guide and both are now guided through the incision and the fleshy parts until the surface of the fixator plate is reached; the trocar is withdrawn and the inner tubular guide is inserted into the outer guide and pushed inwardly until its reduced diameter portion enters the corresponding bore in the plate. In order to enable full contact between the outer guide and the plate the guide is preferably cut off at a corresponding angle. A thin drill rod or guide wire is inserted into the small bore of the inner guide and is rotated by a suitable tool so as to penetrate the bone, the marrow and to enter the spherical head into which it penetrates as far as the compact bony parts at the head's inner end. The operation is continuously controlled by viewing it on a television screen in a known manner, and in case the position of the guide wire is correct both in regard to the depth of penetration and angular position, the drill or guide wire is withdrawn, and a second, larger diameter drill is inserted, of a size somewhat smaller than the outer thread of the screw to be inserted. The drill is either provided with a shaft corresponding to the inner diameter of the outer guide, or an intermediate tube is inserted into the guide guiding the drill absolutely concentrical with the guide axis. After drilling, a screw is inserted into the bore through the outer tubular guide and driven into the bone material by means of a screw driver, until the screwhead encounters the fixator plate and assists in pulling the fractured parts together. Now the outer guide is removed and the screw and the fixator plate are now in correct position on the femur shaft. The plate is now additionally fastened to the shaft by means of one perpendicular screw passing through the tool grip, the skin and the tissue, and through the plate into the bone material. This operation is similarly executed, but the guides, the drill and the screw are obviously of shorter length than their counterparts for the oblique bore. Now a second oblique screw is inserted into the femur head by a similar operation as the first, and thereafter one or more additional shaft screws. After all necessary screws have been inserted and securely fastened in the bone and tightened against the fixator plate, the angular tool is detached from the plate by unscrewing the long screw from the outside, and by pulling the connector arm away. The incisions can now be closed by clamping or sewing in the normal way.

Figure 5:
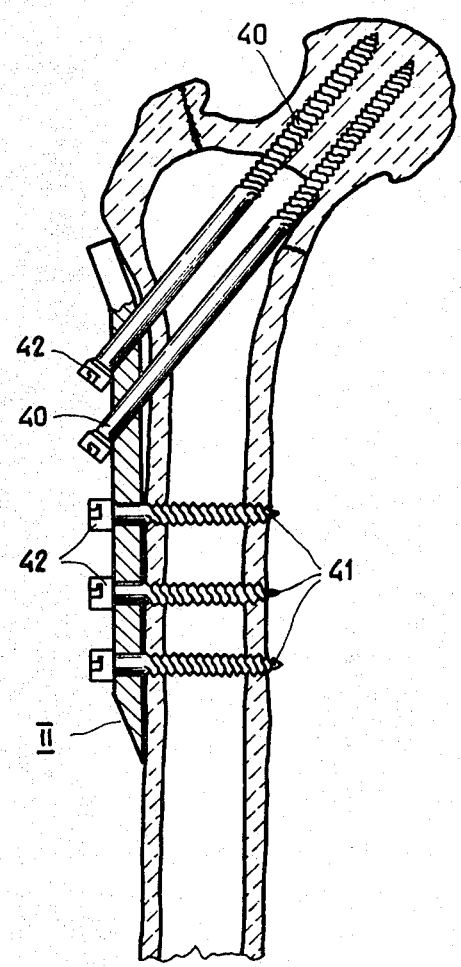
Figure 7:
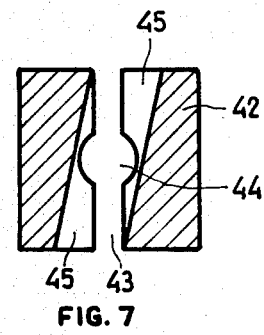
Figure 6:
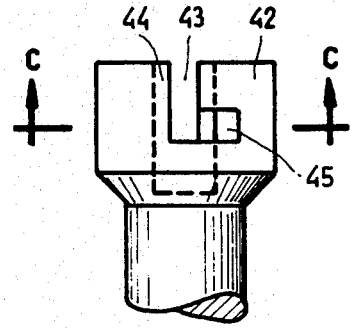
Figure 8:
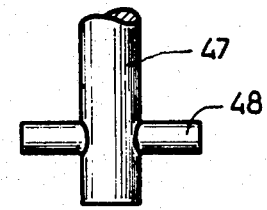

The novel features of the surgical device which are considered as characteristic for the invention are set forth in particular in the appended claims. The invention itself, however, both as to its construction and its method of operation, will be best understood from the following description of a specific embodiment when read in connection with the accompanying drawings, wherein FIG. 1 is a vertical section through an angular auxiliary tool connected to a connector plate, FIG. 2 is a side view of the tool of FIG. 1 viewed along the arrows A—A, FIG. 3 is a second side view of the tool of FIG. 1 viewed along the arrows B—B, showing in addition, the inside of a fixator plate, FIG. 4 is a longitudinal section through a femur and the device showing two stages of the operation with one guide wire and one screw in position, FIG. 5 is a longitudinal section through a femur after completion of the operation, FIG. 6 is a side view of the head of one of the screws used as connectors, FIG. 7 is a section along C—C of FIG. 6, and FIG. 8 is an elevation of a screw extraction tool.

Referring now to FIGS. 1, 2 and 3 of the drawings an angular tool I comprises a straight grip 10 and a connector arm 11 extending at right angles from the top of the grip. The connector arm 11 is bent downwardly at its inner end in the shape of a lug 12 having a contour corresponding to the shape of the upper, bent portion 21 of a fixator plate II. The tool is brought into its shape by bending a straight bar of rectangular cross section, its front being wider than the sides; the sides of the grip portion are shaped wavelike so as to offer a firmer grip, and in order to distinguish the grip from the fixator plate while viewed on an X-ray photo. The fixator plate II comprises a straight, vertical portion 20 and the above, outwardly bent upper portion 21. The tool and the plate of the present embodiment are interconnected in an alignment which ensures absolute parallelism of the grip and the plate, with the aid of the contacting surfaces of the parts 12 and 21, and by means of a long screw 13 which passes through a longitudinal bore along the connector arm into a tapped hole 22 in the top of the fixator plate. The two parts are kept additionally in firm position by two pins 15 firmly attached to the lug 12 and engaging with corresponding holes in the upper part of the plate. The screw 13 is adapted to be screwed and unscrewed in the hole 22 by means of a butterfly grip 14 at its outer end. The grip and the plate are perforated by a number of smooth bores which are co-axially aligned whenever the two components are rigidly connected, a fact indicated by the five centre lines shown in FIG. 1. All bores in the tool grip are of uniform diameter, the bores in the grip being of larger diameter than those in the fixator plate, the latter corresponding to the diameters of the connecting screws.

The bores comprise two obliquely positioned bores 16 and 26 respectively which form an angle of 140°±15° with the frontal planes of both the grip and the plate, and the three bores 17 and 27 respectively which extend perpendicular to the frontal planes. The oblique holes penetrate the fixator plate close to its upper end and pass through the grip close to its bottom end, while the perpendicular holes occupy a relatively comparatively large stretch of both components.

FIG. 4 illustrates additional components of the device and its application in setting and connecting a fractured upper femur. They comprise one long tubular guide assembly adapted to be inserted into the obliquely extending bores, and at least one shorter tubular guide assemblies for insertion into the perpendicularly extending bores. The latter are not shown for the reason that they are employed only after the long guide assembly has been withdrawn out of the device. Each guide assembly comprises an outer guide 30 and an inner guide 31: each outer guide 30 is in the shape of a thin-walled tube having an outer diameter corresponding to the bores 16 and 17 in the grip portion; its outer end is straight while its inner end is cut off at an angle of 140°±15° so as to contact the fixator plate along its entire edge. The inner guide is also tubular, having a small diameter bore and an outer diameter corresponding to the inner diameter of the guide 30 into which it can be slidingly inserted. The outer diameter of the inner guide is, at the inner end, reduced to the diameter of the bores in the fixator plate 32 into which this end is inserted during operation of a small diameter drill.

The drawing also illustrates two stages of the operation of the tool in connecting a fractured upper part of a femur. As can be clearly seen in regard to the lower guide assembly, a small diameter drill 33 passes through the bore of the inner guide 31 and has been inserted into the bony part of the spherical head by rotational movement given to it from the outside, e.g. by an electric drill. This operation is initially carried out through one guide assembly and the upper assembly is drawn to illustrate the final stage, wherein a screw 40 has been driven into the bone as far as its head allows after having contacted the outer surface of the plate II. As described in the foregoing, the drills 33 are inserted into the bone and, in case their position is satisfactory, they are withdrawn together with the inner tubular guides. However, should the surgeon observe that their position is not suitable for the insertion of the connecting screws, the fixator plate is brought into another position on the bone surface by means of the tool, and drilling is repeated. After the drills and the inner guides have been removed, a larger-diameter drill is inserted through the bore of the outer tubular guide, into the pre-drilled holes and is rotated so as to enlarge these holes to a diameter smaller than the screw thread on the connector screws. After completion of this operation a screw 40 is inserted into the bore through the outer guide and is rotated by means of a long screw driver, whereby the fractured ends are pulled together by being supported by the fixator plate against which the screw heads abut.

After one screw 40 has been fastened, the outer guide 30 is withdrawn from the bore, making room for the insertion of a perpendicular guide assembly through one of the bores 17 and 27. These guides are shorter, but of the same construction, and are not shown in the drawing for the above reasons. It is noted, however, that the inner ends of the outer tubular guides are cut off straight and not at a slant as before.

The drilling and screwing operations are similarly executed for each bore until all five screws are in place, as indicated in FIG. 5 of the drawings. The drawing shows the fixator plate II, tow obliquely inserted screws 40 and three perpendicular screws 41. Regarding the insertion of the three screws 41 it will be noted that it may be possible to use one set of guides for consecutive insertion of the three screws, or three sets for simultaneous insertion.

In the drawings the tissue and the skin surrounding the bone have been omitted, for the sake of clearness, but it will be understood that the insertion of the guide assemblies requires making small incisions in the skin which are subsequently closed by sewing or clamping.

FIGS. 6 and 7 illustrate a novel embodiment of the screwheads permitting ready withdrawal of the screws out of the bone in which they are embedded, with the aid of a special tool. The heads 42 of both the screws 40 and 41 are square, but they may be of cylindrical or hexagonal cross section as long as they are freely movable along the inner bore of the outer guide 30. The head shown in FIGS. 5 and 6 is crossed by a straight slot 43 which serves for inserting therein a conventional screw driver for driving it into the bone.

A central bore 44 of larger diameter than the slot's width penetrates the head beyond the slot's depth, and the slot is widened in its bottom portion by an obliquely extending recess 45, the bore and the recess permitting the insertion of a withdrawal tool shown in FIG. 8. This tool consists of a straight cylindrical shaft 47 which is cross-wise penetrated, close to its bottom, by a pin 48.

For withdrawing a screw the tool shaft is inserted into the bore 44 and turned in anti-clockwise direction whereby the ends of the pin 48 engage with the recesses 45. Thereby the screw is rotated and pulled out of the bone, a task which would be very hard by using a conventional screwdriver.

The embodiment described in the foregoing in connection with the accompanying drawings constitutes a configuration which has proved itself advantageous for operating various fractures of the upper part of the femur. The invention is, however, not limited to this embodiment alone, which may be varied and modified to suit various applications.

It is, for instance, not necessary that the grip 10 and the plate II are parallel: to the contrary, they may diverge or converge, as long as the corresponding bores through the two components are coaxial. Similarly, the connector arm 11 may be of different configuration, as long as it can serve for rigid and firm attachment of the plate II. On the other hand, two oblique and three perpendicular screws are generally sufficient as connecting members, but it will be understood that the tool and the fixator plate may be adapted for a larger or smaller number of screws, by drilling more bores than shown in the present drawings, but using eventually a smaller number of screws.

The angle of 140° is suitable for most femur heads, but it may be advisable to prepare a tool and several fixator plates for an angle of 135°, and similar units for an angle of 145°, which may then be used for special cases.

I claim:

1. A surgical device for percutaneous connection of a fractured upper portion of the femur, comprising: at least one long screw for angular insertion into said femur head and at least two shorter screws to be inserted into said femur shaft, each of said screws comprising a head and a screw-threaded shaft; a fixator plate adapted to be fastened to said femur, provided with a screw threaded bore in its head portion which is close to said femur head, with a plurality of bores of a diameter corresponding to said screw shafts, whereof at least one angularly extending bore, intended to receive said long screw, forms an angle of 140°±15° with the plane of said fixator plate, and whereof at least two bores, intended to receive said shorter screws, are perpendicular to the plane of said fixator plate, the lower end of said fixator plate being sharpened in chisel fashion; an auxiliary tool comprising a grip portion substantially parallel to said fixator plate and a connector arm extending from the top of said grip portion to the top of said fixator plate, said connector arm being provided with screw means adapted to engage with said threaded bore in said fixator plate and with means adapted to prevent rotational dislocation of said fixator plate in respect of said connector arm, said grip portion being provided with a plurality of bores coaxially aligned with said bores in said fixator plate after this plate is firmly connected to said auxiliary tool, said bores being of a diameter somewhat larger than the largest diameter of said screw heads; at least two tubular guide assemblies adapted to penetrate through said bores in said grip portion towards said bores in said fixator plate, each assembly comprising an outer guide of an outer diameter corresponding to the diameter of said bores in said grip portion and an inner diameter permitting the passage therethrough of the heads of said screws, each assembly further comprising an inner guide of an inner diameter permitting the passage therethrough of a small-diameter drill and of an outer diameter corresponding to the inner diameter of said outer guide, the outer diameter of said inner guide being reduced to the diameter of said bores in said fixator plate at its end close to said fixator plate, there being provided at least one long guide assembly adapted for the insertion of said long screw into said femur head, and at least one shorter guide assembly adapted for the insertion of shorter screws into said femur shaft.

2. The device of claim 1 wherein said fixator plate is in the shape of a straight bar of rectangular cross section, whereof the upper portion is bent to form an angle with the main portion.

3. The device of claim 2 wherein said upper portion of said fixator plate is provided with said threaded bore and with two holes adapted to engage with two pins projecting out of the end of said connector arm.

4. The device of claim 3 wherein said connector arm is straight and extends at right angles to said grip portion and to said fixator plate, and wherein its end is bent downwardly in the form of a lug corresponding to the shape of said bent portion of said fixator plate.

5. The device of claim 4 wherein a long screw passes through a longitudinal bore in said connector arm into said threaded bore in said fixator plate.

6. The device of claim 4 wherein two pins are fastened to said lug on said connector arm, corresponding to said two holes in said fixator plate.

7. The device of claim 1 wherein said outer tubular guide is cut off at its end to form an angle of $140° \pm 15°$ with its axis, corresponding to the angle of said bore in said fixator plate.

8. The device of claim 1 wherein the heads of said screws are of square cross section and provided with a slot adapted for the insertion of a screwdriver.

9. The device of claim 8 wherein said slot in said screwhead is enlarged at its bottom to form a recess adapted to receive a withdrawing tool.

* * * * *